(12) United States Patent
Ikeda

(10) Patent No.: US 11,622,673 B2
(45) Date of Patent: Apr. 11, 2023

(54) ENDOSCOPE

(71) Applicant: FUJIFILM Corporation, Tokyo (JP)

(72) Inventor: Toshiyuki Ikeda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 313 days.

(21) Appl. No.: 16/813,688

(22) Filed: Mar. 9, 2020

(65) Prior Publication Data

US 2020/0297188 A1  Sep. 24, 2020

(30) Foreign Application Priority Data

Mar. 20, 2019  (JP) ............................. JP2019-052439

(51) Int. Cl.
 *A61B 1/005* (2006.01)
 *A61B 1/00* (2006.01)

(52) U.S. Cl.
 CPC ........ *A61B 1/0053* (2013.01); *A61B 1/00006* (2013.01); *A61B 1/0055* (2013.01); *A61B 1/0057* (2013.01); *A61B 1/00098* (2013.01)

(58) Field of Classification Search
 CPC . A61B 1/0053; A61B 1/00078; A61B 1/0006; A61B 1/00098; A61B 1/0055; A61B 1/0057
 See application file for complete search history.

(56) References Cited

U.S. PATENT DOCUMENTS

| 3,890,960 | A | * | 6/1975 | Wunsch, nee Kuhn . A61B 1/24 600/192 |
| 4,215,703 | A | * | 8/1980 | Willson .......... A61M 25/09033 604/95.04 |
| 4,329,980 | A | * | 5/1982 | Terada ............... A61B 1/00078 600/140 |
| 4,516,972 | A | * | 5/1985 | Samson ........... A61M 25/0012 604/525 |

(Continued)

FOREIGN PATENT DOCUMENTS

| JP | 2002360505 | 12/2002 |
| JP | 2003-000533 | 1/2003 |

(Continued)

OTHER PUBLICATIONS

"Office Action of Japan Counterpart Application" with English translation thereof, dated Oct. 5, 2021, p. 1-p. 4.

*Primary Examiner* — John P Leubecker
*Assistant Examiner* — Jae Woo
(74) *Attorney, Agent, or Firm* — JCIPRNET

(57) ABSTRACT

Provided is an endoscope allowing two operating methods, that is, a surgeon's own manual operation and an operating method using a hand other than the surgeon regarding a hardness adjusting operation. An endoscope includes an insertion part having a flexible part; an operating part continuously provided on a proximal end side of the insertion part; a hardness adjusting mechanism serving as a first driving force input member that is provided from the oper- (Continued)

ating part to the flexible part and adjusts the hardness of the flexible part; an operating ring that is provided in the operating part and is manually operated and inputs a driving force to the hardness adjusting mechanism; and a shaft serving as a second driving force input member that is provided separately from the operating ring and inputs a driving force to the hardness adjusting mechanism.

8 Claims, 6 Drawing Sheets

(56) References Cited

U.S. PATENT DOCUMENTS

| | | | | |
|---|---|---|---|---|
| 5,003,918 | A * | 4/1991 | Olson | A61B 17/320758 156/425 |
| 5,125,395 | A * | 6/1992 | Adair | A61B 18/26 604/95.01 |
| 5,487,757 | A * | 1/1996 | Truckai | A61M 25/0144 604/95.04 |
| 5,611,777 | A * | 3/1997 | Bowden | A61M 25/0136 604/95.01 |
| 5,810,715 | A * | 9/1998 | Moriyama | A61B 1/00078 600/141 |
| 5,885,208 | A * | 3/1999 | Moriyama | A61B 1/0051 600/146 |
| 6,203,494 | B1 * | 3/2001 | Moriyama | A61B 1/00078 600/149 |
| 6,261,246 | B1 * | 7/2001 | Pantages | A61B 8/4461 600/463 |
| 6,471,641 | B2 * | 10/2002 | Sakamoto | A61B 1/0055 600/141 |
| 7,892,166 | B2 * | 2/2011 | Long | A61B 5/065 600/149 |
| 7,896,801 | B2 * | 3/2011 | Uchimura | A61B 1/00071 600/131 |
| 8,083,879 | B2 * | 12/2011 | Swinehart | F16C 1/20 604/95.04 |
| 8,366,606 | B2 * | 2/2013 | Watanabe | A61B 1/00078 600/114 |
| 9,839,345 | B2 * | 12/2017 | Ueda | A61B 1/0057 |
| 10,653,303 | B2 * | 5/2020 | Asaoka | A61B 1/0055 |
| 10,925,470 | B2 * | 2/2021 | Okaniwa | A61B 1/0055 |
| 2005/0272976 | A1 * | 12/2005 | Tanaka | A61B 1/0016 600/114 |
| 2006/0100484 | A1 * | 5/2006 | Maeda | A61B 1/0051 600/152 |
| 2007/0149852 | A1 * | 6/2007 | Noguchi | A61B 1/0055 600/152 |
| 2007/0173693 | A1 * | 7/2007 | Refael | A61B 1/0055 600/152 |
| 2007/0249932 | A1 * | 10/2007 | Shahinian | A61B 34/70 600/421 |
| 2008/0125628 | A1 * | 5/2008 | Ueno | G02B 23/2476 600/130 |
| 2008/0243064 | A1 * | 10/2008 | Stabler | A61B 34/30 604/95.01 |
| 2009/0018566 | A1 * | 1/2009 | Escudero | A61B 17/320758 606/159 |
| 2009/0187131 | A1 * | 7/2009 | Fitzgerald | A61M 1/0003 604/119 |
| 2010/0324370 | A1 * | 12/2010 | Dohi | A61M 25/0043 600/144 |
| 2011/0040308 | A1 * | 2/2011 | Cabrera | A61B 17/00234 606/144 |
| 2011/0071347 | A1 * | 3/2011 | Rogers | A61B 34/71 600/114 |
| 2011/0071543 | A1 * | 3/2011 | Prisco | A61B 90/92 600/118 |
| 2011/0230712 | A1 * | 9/2011 | Matsuura | A61B 1/018 600/106 |
| 2012/0029281 | A1 * | 2/2012 | Frassica | A61B 1/00135 600/114 |
| 2012/0053417 | A1 * | 3/2012 | Yamakawa | A61B 1/00078 600/144 |
| 2012/0238804 | A1 * | 9/2012 | Yamakawa | A61B 1/00135 600/101 |
| 2013/0041222 | A1 * | 2/2013 | Moriyama | A61B 1/00154 600/114 |
| 2014/0135580 | A1 * | 5/2014 | Omoto | A61B 1/00039 600/146 |
| 2014/0180122 | A1 * | 6/2014 | Stigall | A61B 5/6852 600/478 |
| 2015/0087905 | A1 * | 3/2015 | Ueda | A61B 1/005 604/95.04 |
| 2015/0119638 | A1 * | 4/2015 | Yu | A61B 1/018 600/102 |
| 2015/0250547 | A1 * | 9/2015 | Fukushima | G05B 15/02 606/130 |
| 2016/0276085 | A1 * | 9/2016 | Matsuki | H01F 13/003 |
| 2017/0127910 | A1 * | 5/2017 | Asaoka | A61B 1/0052 |
| 2019/0099064 | A1 * | 4/2019 | Nakamura | A61B 1/00078 |
| 2019/0117942 | A1 * | 4/2019 | Williams | B25J 9/06 |
| 2019/0254506 | A1 * | 8/2019 | Hamm | A61B 1/04 |
| 2019/0313885 | A1 | 10/2019 | Okita | |
| 2020/0000315 | A1 * | 1/2020 | Takahashi | A61B 1/0005 |
| 2020/0000316 | A1 * | 1/2020 | Ikeda | A61B 1/0051 |
| 2020/0100647 | A1 * | 4/2020 | Craig | A61B 1/0005 |
| 2020/0188639 | A1 * | 6/2020 | Stigall | A61B 1/00078 |
| 2020/0345217 | A1 * | 11/2020 | Tearney | A61B 5/0073 |
| 2020/0360100 | A1 * | 11/2020 | Mantri | A61B 90/361 |

FOREIGN PATENT DOCUMENTS

| | | |
|---|---|---|
| JP | 2012050557 | 3/2012 |
| JP | 2013027466 | 2/2013 |
| WO | 2017043124 | 3/2017 |
| WO | 2018096679 | 5/2018 |

* cited by examiner

ENDOSCOPE

CROSS-REFERENCE TO RELATED APPLICATION

This application claims priority under 35 USC 119 from Japanese Patent Application No. 2019-052439 filed on Mar. 20, 2019, the disclosure of which is incorporated by reference herein in its entirety.

BACKGROUND OF THE INVENTION

1. Field of the Invention

The present disclosure relates to an endoscope.

2. Description of the Related Art

Endoscopes are known that include an insertion part having a flexible part and that can adjust the hardness of the flexible part by compressing a hardness adjusting member, such as a coil provided within the insertion part. In the related art, in a case where an endoscope is inserted into, for example, the body of a subject, such as a patient, a surgeon, such as a doctor, performs the insertion while manually operating an operating ring or the like provided in an operating part and adjusting the hardness of the flexible part.

Additionally, an attempt has been made to motor-operate the harness adjustment of the flexible part of the endoscope, using a hardness adjusting mechanism driven by an actuator or the like.

For example, JP2003-000533A discloses an endoscope apparatus in which a wire secured to the vicinity of a distal end part of a coil inserted through an insertion part is pulled by a power device, such as an actuator (motor), to compressively deform the coil and change the hardness of the insertion part.

SUMMARY OF THE INVENTION

Meanwhile, in addition to the skill required by a surgeon, various kinds of work are involved in an endoscopic procedure. For this reason, there are cases where, as long as it is more appropriate for the surgeon to perform a hardness adjusting operation, it is more appropriate to borrow a hand other than the surgeon in order to reduce the work burden on the surgeon.

As methods of borrowing a hand other than the surgeon, as in the endoscope described in JP2003-000533A, in addition to a method of performing the hardness adjusting operation using the actuator, a method of leaving the hardness adjusting operation to an assistant who assists the surgeon even in a case where no actuator is used is also conceivable.

However, in the endoscope described in JP2003-000533A, the hardness adjusting operation can only be performed by using the actuator, and the surgeon himself/herself cannot perform the hardness adjusting operation. On the other hand, in related-art general endoscopes in which the hardness adjusting operation is performed only by the surgeon's own manual operation, the hardness adjusting operation can only be performed by the surgeon himself/herself, and a hand other than the surgeon cannot be borrowed.

The present disclosure has been made in view of the above circumstances, and an object thereof is to provide an endoscope allowing two operating methods, that is, a surgeon's own manual operation method and an operating method of asking for another's help other than the surgeon regarding a hardness adjusting operation.

An endoscope according to a first aspect of the present disclosure comprises an insertion part having a flexible part; an operating part continuously provided on a proximal end side of the insertion part; a hardness adjusting mechanism that is provided from the operating part to the flexible part and adjusts the hardness of the flexible part; a first driving force input member that is provided in the operating part and is manually operated to input a driving force to the hardness adjusting mechanism; and a second driving force input member that is provided separately from the first driving force input member to input a driving force to the hardness adjusting mechanism.

According to the above configuration, since the second driving force input member is provided separately from the manually operated first driving force input member, two operating methods, that is, a surgeon's own manual operating method and an operating method using a hand other than the surgeon are allowed regarding the hardness adjusting operation.

An endoscope according to a second aspect of the present disclosure is the endoscope according to the first aspect, further comprising a connection interface to which an external mechanism, which inputs a driving force to the second driving force input member, is attachably and detachably connected.

According to the above configuration, the driving force can be supplied to the hardness adjusting mechanism by the external mechanism via the second driving force input member. Here, since the external mechanism is attachably and detachably connected to the connection interface, the external mechanism can be attached and detached as necessary, and appropriate usage is possible depending on procedures.

An endoscope according to a third aspect of the present disclosure is the endoscope according to the second aspect in which the first driving force input member is manually operable regardless of whether or not the external mechanism is connected to the connection interface.

According to the above configuration, even in a state where the external mechanism is connected to the connection interface, the surgeon can adjust the hardness of the flexible part by the manual operation.

An endoscope according to a fourth aspect of the present disclosure is the endoscope according to the third aspect in which the external mechanism is an actuator.

According to the above configuration, the hardness of the flexible part can be adjusted by a motor operation by the actuator via the second driving force input mechanism.

An endoscope according to a fifth aspect of the present disclosure is the endoscope according to the second aspect, further comprising a transmission member that transmits the driving force, which is input from the first driving force input member, to the hardness adjusting mechanism, in which the second driving force input member is connected to the transmission member.

According to the above configuration, the driving force from the first driving force input member and the driving force from the second driving force input member can be transmitted to the hardness adjusting mechanism via the transmission member. Accordingly, compared to a configuration in which the transmission member, which transmits the driving force from the second driving force input member, is provided separately from the transmission member that transmits the driving force from the first driving force input member, the number of parts can be reduced, and a decrease in the size of the endoscope can be suppressed.

An endoscope according to a sixth aspect of the present disclosure is the endoscope according to the fifth aspect in which the second driving force input member is a shaft, and the shaft is connected to the transmission member via the speed reduction mechanism that reduces the driving force from the external mechanism.

According to the above configuration, since the second driving force input member is the shaft, the driving force of the external mechanism can be stably transmitted to the transmission mechanism as compared to a case where the second driving force input member is a tube or the like. Additionally, since the shaft is connected to the transmission member via the speed reduction mechanism, the hardness of the flexible part can be adjusted with a small driving force as compared to a configuration in which the shaft is connected to the transmission member without using the speed reduction mechanism.

An endoscope according to a seventh aspect of the present disclosure is the endoscope according to the fifth aspect or the sixth aspect, the hardness adjusting mechanism includes a tightly wound coil spring provided in the insertion part; a wire inserted into the tightly wound coil spring and secured to a distal end of the tightly wound coil spring; and a movable member that is engaged with the transmission member and compresses the tightly wound coil spring by separating a proximal end of the tightly wound coil spring and a proximal end of the wire from each other.

According to the above configuration, the hardness of the flexible part can be adjusted by separating the proximal end of the tightly wound coil spring and the proximal end of the wire from each other by the movable member engaged with the transmission member to compress the tightly wound coil spring.

An endoscope according to an eighth aspect of the present disclosure is the endoscope according to the seventh aspect in which the tightly wound coil spring is compressed by fixing the proximal end of the wire and pressing the proximal end of the tightly wound coil spring by the movable member.

According to the configuration, the hardness of the flexible part can be adjusted by moving the proximal end of the tightly wound coil spring and the proximal end of the wire from each other to compress the tightly wound coil spring.

According to the present disclosure, the two operating methods, that is, the surgeon's own manual operation and the operating method using a hand other than the surgeon are allowed regarding the hardness adjusting operation.

DESCRIPTION OF THE PREFERRED EMBODIMENTS

Figure 1:
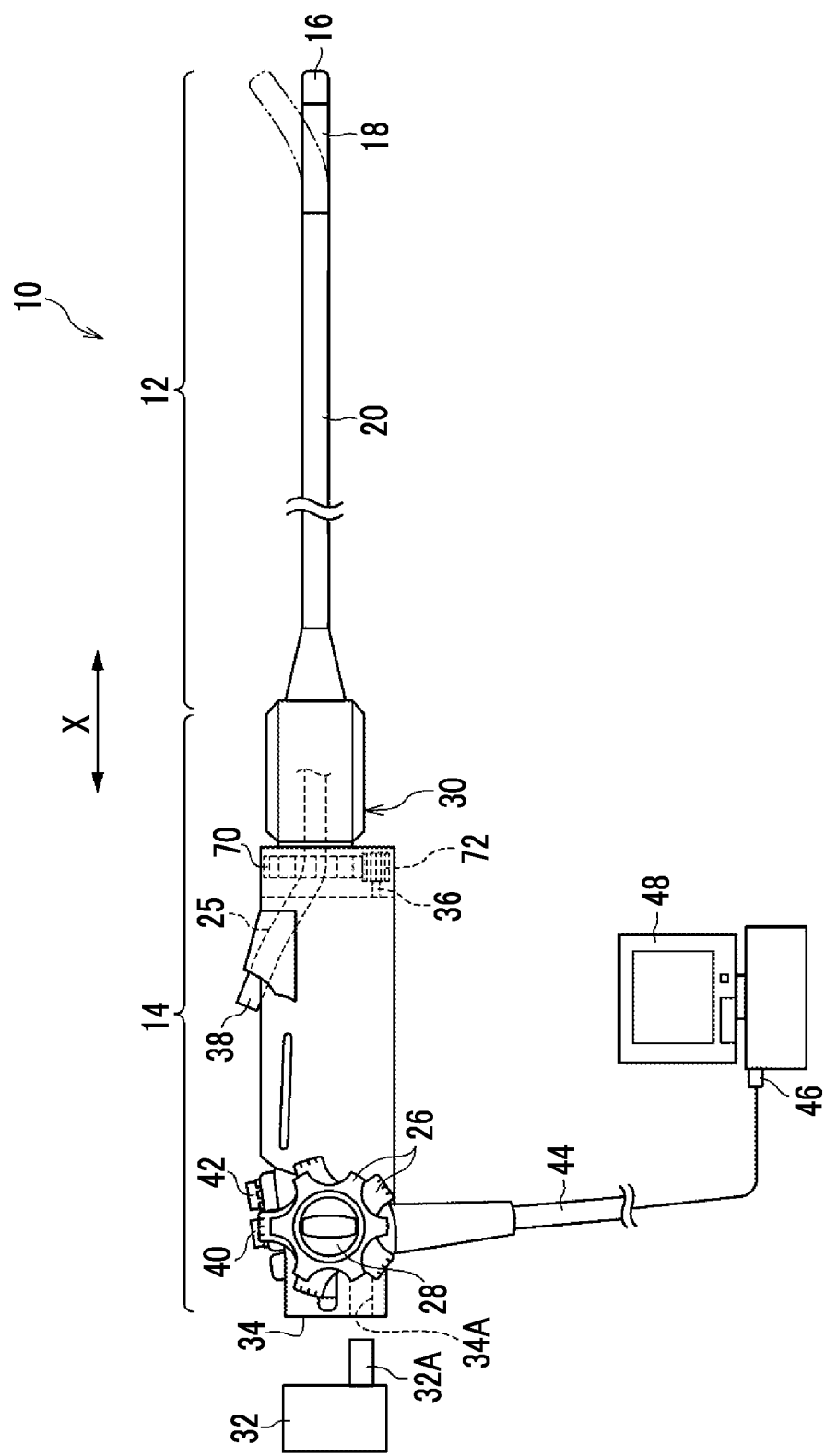
FIG. 1 is an overall schematic view illustrating an endoscope according to an example of an embodiment.

Hereinafter, an endoscope according to an example of an embodiment of the present disclosure will be described with reference to the drawings. In addition, in the drawings, arrow X indicates an axial direction of an insertion part of the endoscope.

Entire Configuration of Endoscope

An endoscope 10 according to the present embodiment is, for example, a medical endoscope that is inserted into a lumen in order to perform treatment or examination of the body of a subject (specifically, the digestive tracts, such as the stomach and the large intestine), and performs treatment, such as collection of biological tissue of an imaging or examination target region within the lumen.

As illustrated in FIG. 1, the endoscope 10 has an insertion part 12 and an operating part 14 provided continuously with the insertion part 12. In addition, hereinafter, a side where the insertion part 12 of the endoscope 10 is provided (a right side in FIG. 1) will be referred to as a "distal end side", and a side where the operating part 14 of the endoscope 10 is provided (a left side in FIG. 1) is referred to as a "proximal end side".

Configuration of Insertion Part

The insertion part 12 is an elongated region to be inserted into the body, and has a hard distal end part 16 provided on the distal end side (that is, an end side opposite to the operating part 14), a bendable bending part 18 connected to the distal end part 16, and a flexible part 20 connected to the bending part 18.

An imaging unit (not illustrated) formed by integrally unitizing a charge coupled device (CCD) sensor, a complementary metal oxide semiconductor (CMOS) sensor, an imaging lens, and the like are incorporated in the distal end part 16. Additionally, the distal end part 16 is also provided with an illumination lens (not illustrated) for irradiating an observation region with illumination light, a forceps outlet (not illustrated) for inserting forceps for collecting biological tissue, a nozzle (not illustrated) for supplying air and water, and the like.

Figure 2:
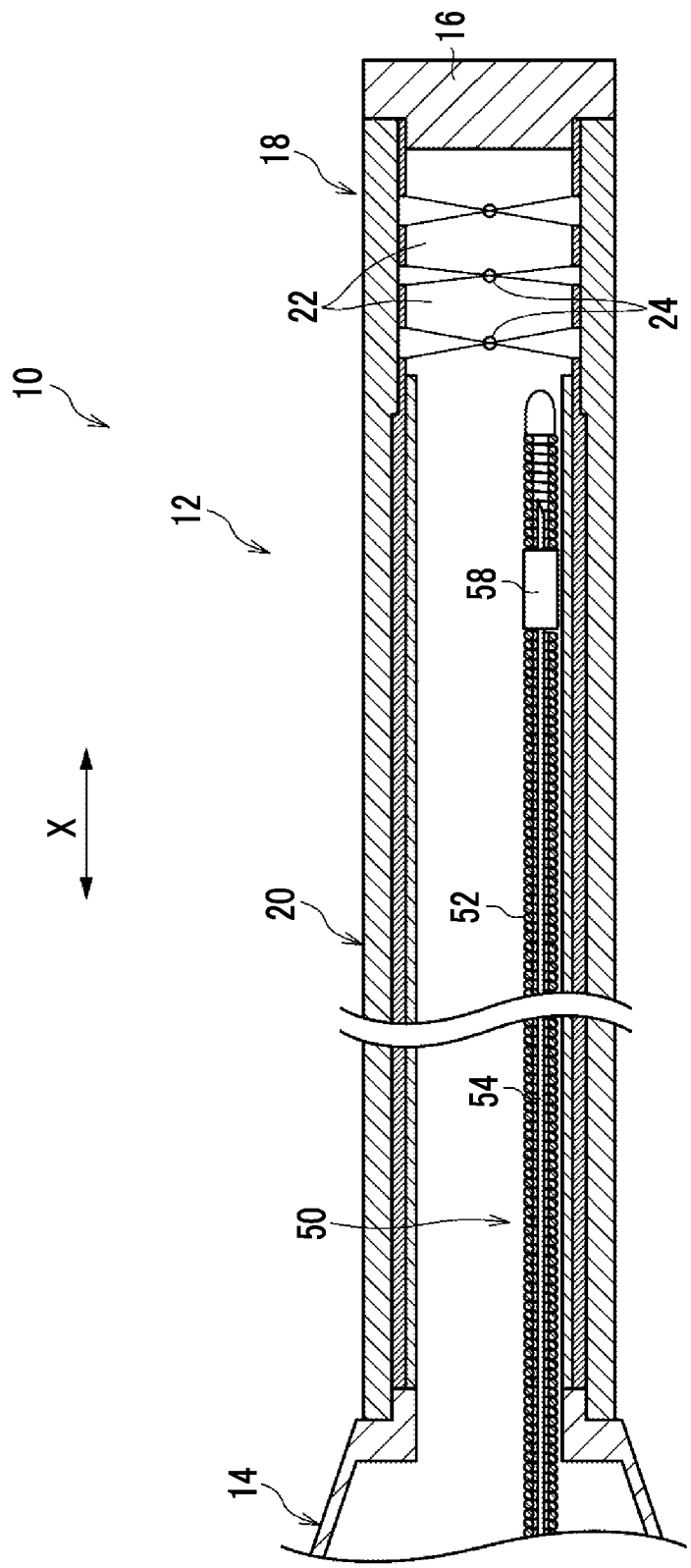
FIG. 2 is a partially cross-sectional view illustrating an internal configuration of an insertion part of the endoscope illustrated in FIG. 1.

The bending part 18 is, for example, a region that bends in four directions, up and down and left and right, in order to insert the distal end part 16 into the body and direct the distal end part toward an observation region. As illustrated in FIG. 2, as an example, the bending part 18 includes a plurality of substantially cylindrical bending pieces 22 and a plurality of pins 24 that couple the bending pieces 22 to each other, and the bending pieces 22 adjacent to each other with a pin 24 as an axis are connected to each other so as to be rotationally movable.

The flexible part 20 is a region that connects the distal end part 16 and the bending part 18 and the operating part 14 to each other and is an elongated tube having flexibility.

Built-in objects including a forceps channel 25, an air/water supply channel (not illustrated), a signal line (not illustrated), a light guide (not illustrated), and the like are inserted through the flexible part 20 (and the bending part 18). Additionally, a hardness adjusting mechanism 50 (refer to FIG. 3), which will be described below, for adjusting the hardness of the flexible part 20 is provided inside the flexible part 20.

Configuration of Operating Part

The operating part 14 is a region for operating the endoscope 10, and has a pair of operating knobs 26 that performs a bending operation of the bending part 18 of the insertion part 12, as illustrated in FIG. 1. A rotating member (not illustrated), such as a sprocket, which is rotated with the rotation of the operating knob 26, is provided inside the operating part 14, and, for example, a pair of bending operating wires (not illustrated) via a chain or the like is wound around the rotating member.

Additionally, end parts of the bending operating wires on the distal end side is inserted through a guide part (not illustrated) provided inside the pins 24 of the bending part 18 and is fixed to the distal end part. Accordingly, by manually operating the operating knob 26 to rotate the rotating member, one of the pair of bending operating wires is wound up via the chain and pulled to the proximal end side, and the other is fed to the distal end side.

That is, the bending part 18 is configured to be bent in a pulling direction of the bending operating wires by moving the pair of bending operating wires forward and backward by the operating knob 26. In addition, the operating knob 26 is provided with a lock 28 for holding the bending part 18 in a bent state.

Additionally, the operating part 14 is provided with an operating ring 30 serving as a first driving force input member. The operating ring 30 is a cylindrical member that is attached to an outer peripheral surface of the operating part 14 so as to be rotatable around the axis of the insertion part 12, and allows a driving force to be input to the hardness adjusting mechanism 50 (refer to FIG. 3), which will be described below, by being manually operated by a surgeon.

Moreover, the operating part 14 is provided with a connection interface 34 to which an actuator 32 serving as an example of an external mechanism is attachably and detachably connected. In addition, the operation of the actuator 32 can be performed by, for example, a pedal operation with a foot or a voice input, and the surgeon can operate without using his/her hand.

Figure 3:
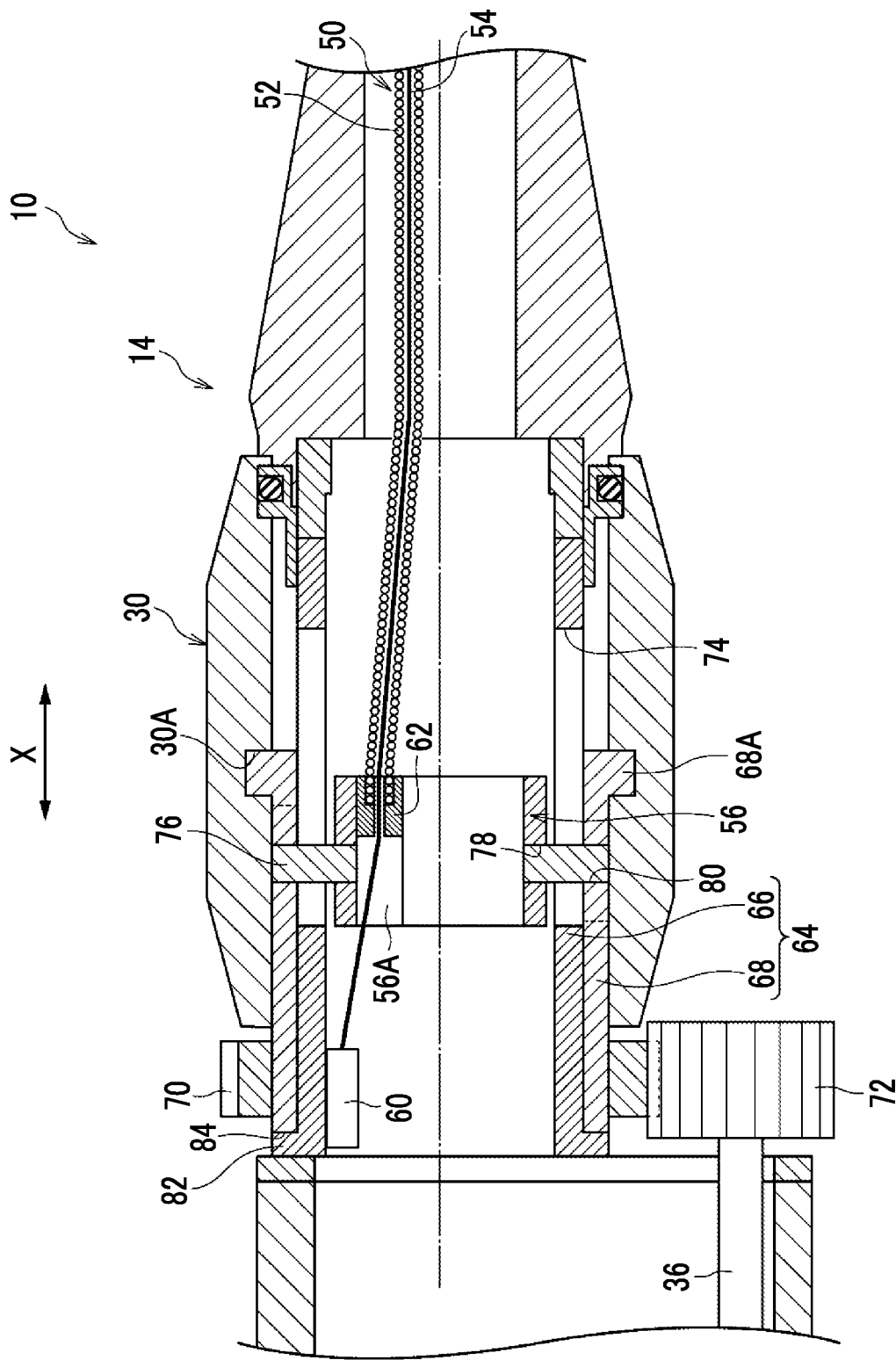
FIG. 3 is a partially cross-sectional view illustrating an internal configuration of an operating part of the endoscope illustrated in FIG. 1.

The connection interface 34 is formed with an insertion hole 34A into which a drive shaft 32A of the actuator 32 is inserted. Meanwhile, as illustrated in FIG. 3, the operating part 14 is provided with a shaft 36 serving as a second driving force input member in which a connection recess (not illustrated) is formed on an end surface on the proximal end side facing the insertion hole 34A. Accordingly, the drive shaft 32A of the actuator 32 is connected to the connection recess of the shaft 36 through the insertion hole 34A, so that the driving force of the actuator 32 can be input to the hardness adjusting mechanism 50, which will be described below, via the shaft 36.

In addition, it is preferable that the shaft 36 is made of a material with little drive transmission loss due to deformation or the like. Specifically, the shaft 36 is made of, for example, a material, such as a metal, having a higher bending stiffness than a resin or the like.

Additionally, as illustrated in FIG. 1, the operating part 14 is provided with a forceps insertion port 38 for communicating with the forceps outlet (not illustrated) of the distal end part 16 of the insertion part 12 and the forceps channel 25 of the flexible part 20 and for inserting a treatment tool, such as the forceps. Moreover, a suction button 40 for performing suction through the forceps channel 25 from the forceps outlet of the distal end part 16, an air/water supply button 42 for supplying air and water through an air/water supply channel (not illustrated) of the flexible part 20 from the nozzle (not illustrated) provided at the distal end part 16, and the like are disposed.

In addition, the operating part 14 of the endoscope 10 is provided with various switches (not illustrated) for observing or capturing an image with the imaging unit, such as a zoom switch, a still image capturing switch, and a freeze switch.

Additionally, a universal cord 44 is connected to the operating part 14. The water/air supply channel, a suction channel, the light guide, the signal line, and the like (not illustrated) are inserted through the universal cord 44, and the universal cord 44 is connected to an air/water supply device, a light source device, and a processor device (not illustrated) 48, and the like via a connector 46.

Configuration of Hardness Adjusting Mechanism

Next, the configuration of the hardness adjusting mechanism 50, which adjusts the hardness of the flexible part 20, will be specifically described. As illustrated in FIGS. 2 and 3, the hardness adjusting mechanism 50 has a tightly wound coil spring 52, a wire 54 inserted through a hollow part of the tightly wound coil spring 52, and a cylindrical movable ring 56 (refer to FIG. 3) serving as a movable member that compresses the tightly wound coil spring 52.

As illustrated in FIG. 2, the tightly wound coil spring 52 and the wire 54 extend in the axial direction of the insertion part 12 from the operating part 14 to the flexible part 20 of the insertion part 12, and an end part of the wire 54 on the distal end side is secured to an end part of the tightly wound coil spring 52 on the distal end side by a fixing metal fitting 58. In addition, the tightly wound coil spring 52, the wire 54, and the fixing metal fitting 58 are not joined to an inner peripheral surface of the flexible part 20.

As illustrated in FIG. 3, an end part of the wire 54 on the proximal end side is fixed to a support frame 66 (to be described below) provided within the operating part 14 via a sleeve 60. Meanwhile, the end part of the tightly wound coil spring 52 on the proximal end side is held via a sleeve 62 in a holding groove 56A formed on an inner peripheral surface of the movable ring 56 provided within the operating part 14.

For this reason, by moving the movable ring 56 in the axial direction of the insertion part 12 to press the end part of the tightly wound coil spring 52 proximal end side toward the distal end side by the movable ring 56, the end part of the tightly wound coil spring 52 on the proximal end side and the end part of the wire 54 on the proximal end side are separated from each other. Meanwhile, since the movement of a distal end of the tightly wound coil spring 52 is restricted by the fixing metal fitting 58, the tightly wound coil spring 52 is compressed by the movable ring 56. In this way, the hardness of the flexible part 20 can be adjusted by compressing the tightly wound coil spring 52 inserted into the flexible part 20 to increase the bending stiffness of the tightly wound coil spring 52.

Configuration of Drive Mechanism for Movable Ring

Figure 4:
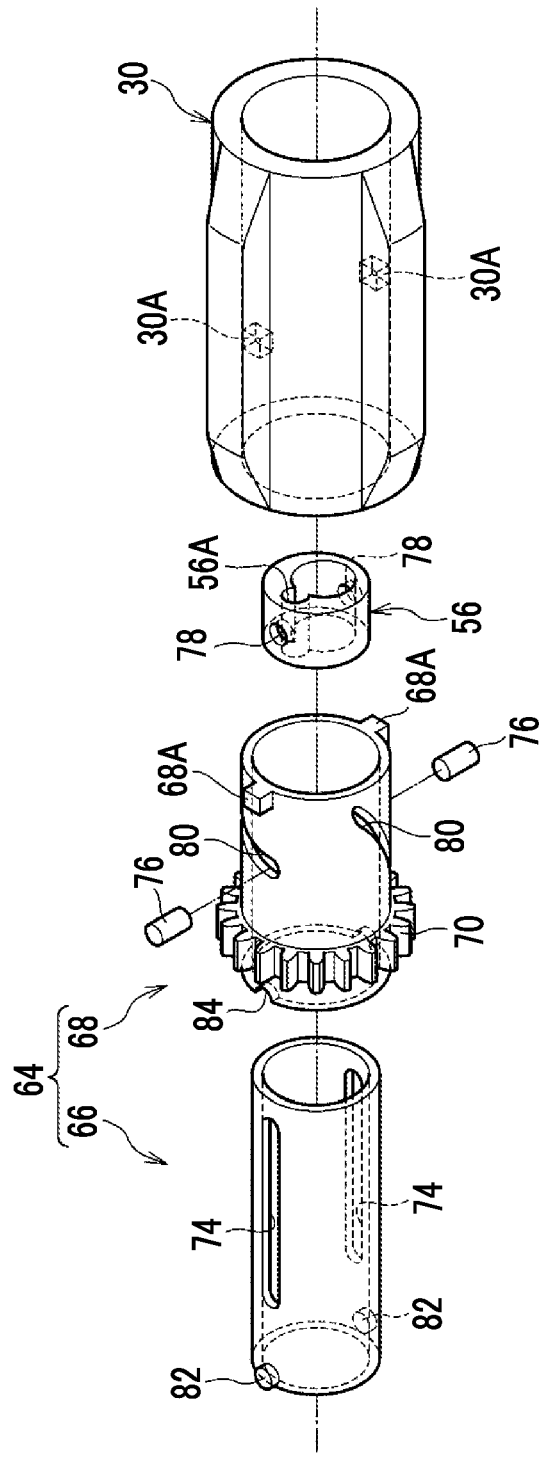
FIG. 4 is an exploded perspective view illustrating an internal configuration of the operating part of the endoscope illustrated in FIG. 1.

Next, an example of an operating mechanism 64, which moves the movable ring 56 of the hardness adjusting mechanism 50 in the axial direction of the insertion part 12, will be specifically described. As illustrated in FIGS. 3 and 4, the operating mechanism 64 has the cylindrical support frame 66 provided on an outer peripheral surface of the movable ring 56 and a cylindrical cam ring 68 serving as a transmission member provided on the outer peripheral surface of the support frame 66. Additionally, the cam ring 68 and the movable ring 56 are disposed so as to be slidable in a circumferential direction and the axial direction of the insertion part 12 along the inner and outer surfaces of the support frame 66.

The operating ring 30 is disposed on an outer peripheral surface of the cam ring 68. A pair of keys 68A, which fits into a pair of key grooves 30A formed in an inner peripheral surface of the operating ring 30, is formed on the outer peripheral surface of the cam ring 68, and the cam ring 68 is made rotatable in conjunction with the rotation of the operating ring 30.

Additionally, a larger-diameter gear 70, which constitutes a speed reduction mechanism, is provided on the outer peripheral surface of the cam ring 68. As illustrated in FIG. 3, the larger-diameter gear 70 is connected to the shaft 36 via a smaller-diameter gear 72 that constitutes the speed reduction mechanism, and the cam ring 68 is made rotatable in conjunction with the rotation of the shaft 36.

Additionally, in a case where the actuator 32 is not driven, the drive shaft 32A is made rotatable by an external force. For this reason, even in a state where the drive shaft 32A (refer to FIG. 1) of the actuator 32 is connected to the shaft 36, the drive shaft 32A rotates together with the shaft 36 in a case where an external force is applied.

In a case where the cam ring 68 is rotated by rotationally operating the operating ring 30, a rotational force also acts on the shaft 36 through the larger-diameter gear 70 and the smaller-diameter gear 72, and the shaft 36 rotates according to the force. For this reason, the cam ring 68 can be rotated by rotating the shaft 36 even in a case where the actuator 32 is not driven.

That is, the operating ring 30 is manually operated regardless of whether or not the actuator 32 is connected to the connection interface 34. In addition, instead of a configuration in which the drive shaft 32A of the actuator 32 is made rotated in a case where the drive shaft is not driven, for example, a clutch (not illustrated) may be provided between the larger-diameter gear 70 and the smaller-diameter gear 72, and the cam ring 68 and the shaft 36 may be brought into a disconnected state by the clutch in a case where the operating ring 30 is operated.

As illustrated in FIGS. 3 and 4, the support frame 66 is formed with a pair of linear grooves 74 having an elongated hole shape in the axial direction (that is, the axial direction of the insertion part 12). Additionally, a pair of first cam pins 76 is respectively engaged with the linear grooves 74 of the support frame 66, and proximal end parts of the first cam pins 76 are respectively inserted into and fixed to the pair of pin holes 78 formed in the movable ring 56.

Meanwhile, the cam ring 68 is formed with a pair of first cam grooves 80 for moving the first cam pins 76 in the axial direction (that is, the axial direction of the insertion part 12) in a case where the cam ring 68 rotates, and distal end parts of the first cam pins 76 are respectively engaged with the pair of first cam grooves 80. That is, the cam ring 68 and the movable ring 56 are engaged with each other by the first cam pins 76 with the support frame 66 interposed therebetween.

Additionally, a pair of second cam pins 82 is provided to protrude from the outer peripheral surface of the support frame 66 on the proximal end side, and the second cam pins 82 are engaged with a pair of second cam grooves 84 formed in the cam ring 68. In addition, the second cam pins 82 are fixing pins that do not move from the fixed position of the support frame 66.

Figure 5:
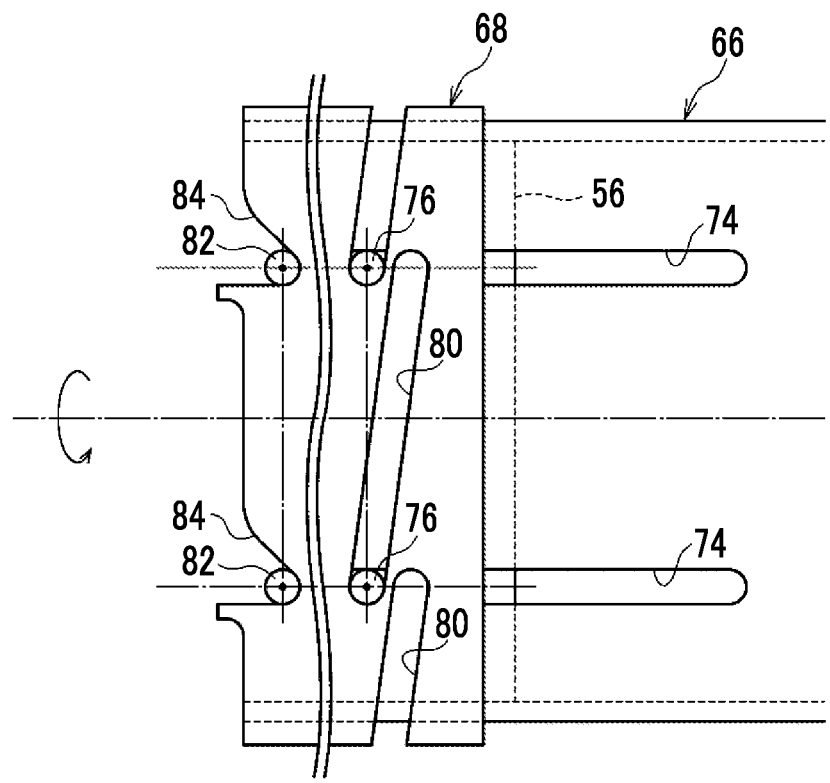
FIG. 5 is a development view illustrating a state before the operation of a drive mechanism of a movable member of the endoscope illustrated in FIG. 1.
Figure 6:
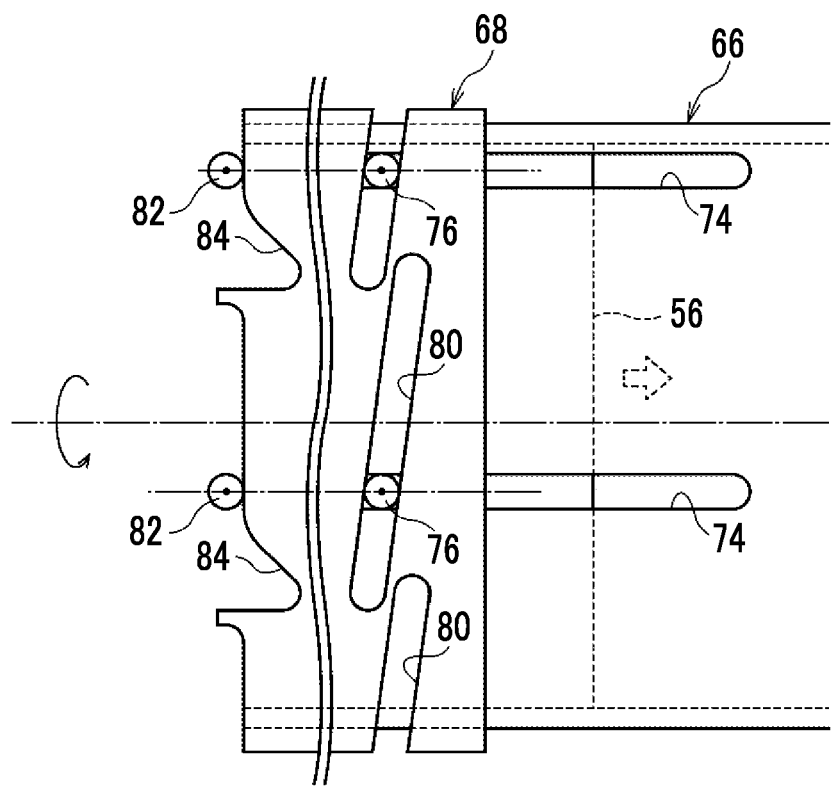
FIG. 6 is a development view illustrating a state during the operation of the drive mechanism of the movable member of the endoscope illustrated in FIG. 1.

In a case where the cam ring 68 is rotated by rotationally operating the operating ring 30 or the shaft 36, as illustrated in FIGS. 5 and 6, the first cam grooves 80 move while being engaging with the first cam pins 76, and the first cam pins 76 are moved in a driven manner along the linear grooves 74 of the support frame 66. Accordingly, the movable ring 56 to which the first cam pins 76 are fixed is also moved forward in the axial direction of the insertion part 12 (that is, moved to the distal end side) with respect to the support frame 66.

Additionally, when the cam ring 68 rotates and the second cam grooves 84 move while being engaged with the second cam pins 82, the cam ring 68 moves forward in the axial direction of the insertion part 12 (that is, moves to the distal end side). In this way, by moving the cam ring 68 and the movable ring 56 forward, the end part of the tightly wound coil spring 52 on the proximal end side is pressed by the movable ring 56, and the tightly wound coil spring 52 can be compressed to harden the flexible part 20.

In addition, the second cam grooves 84 and the second cam pins 82 are provided to increase the amount of forward movement of the first cam pins 76 and the movable ring 56 as compared to a case where the cam ring 68 is rotated at a fixed position by moving the cam ring 68 forward.

Functions and Effects

According to the endoscope 10 of the present embodiment, the shaft 36 for inputting a driving force to the hardness adjusting mechanism 50 is provided separately from the operating ring 30 for inputting the driving force to the hardness adjusting mechanism 50, For this reason, two operating methods, that is, the manual operation of the operating ring 30 by a surgeon himself/herself and the operation of the shaft 36 with another help o other than the surgeon by the actuator 32 or the like, are allowed regarding the hardness adjusting operation.

Additionally, according to the present embodiment, the driving force of the actuator 32 serving as the external mechanism is input to the hardness adjusting mechanism 50 via the shaft 36 serving as the second driving force input member. Therefore, the hardness of the flexible part 20 can be adjusted by a motor operation. Here, since the shaft 36 is made of a material, such as a metal having a higher bending stiffness than a resin or the like, the driving force of the actuator 32 can be stably transmitted to the cam ring 68, compared to a configuration in which the second driving force input member is a flexible member, such as a tube made of a resin.

Additionally, the actuator 32 is attachably and detachably connected to the connection interface 34 formed on the operating part 14 of the endoscope 10. For this reason, the actuator 32 can be attached and detached as necessary, and appropriate usage is possible depending on procedures. Additionally, since the actuator 32 can be detached when not in use, it is possible to suppress the operability from being impaired due to an increase in the size of the operating part 14 of the endoscope 10 in a case where the actuator 32 is not used.

Additionally, for example, in a case where the hardness adjusting operation is electrically performed using only the actuator as in the related-art endoscope, there are possibilities that, in a case where the actuator malfunctions during insertion into the body of the subject, the hardness adjustment operation becomes impossible and the insertion of the endoscope may be hindered.

Here, according to the present embodiment, regardless of whether or not the actuator 32 is connected to the connection interface 34, the surgeon can manually adjust the hardness of the flexible part 20 by operating the operating ring 30. For this reason, it is not necessary to attach and detach the actuator 32 every time the manual operation and the motor operation are switched, and it is possible to easily switch between the manual operation and the motor operation, for example, in an emergency such as a malfunction of the actuator 32.

Additionally, according to the present embodiment, the shaft 36 is connected to the cam ring 68 that transmits a driving force, which is input from the operating ring 30, to the movable ring 56. That is, the driving force from the operating ring 30 and a driving force from the shaft 36 are transmitted to the movable ring 56 via the cam ring 68. For this reason, compared to a configuration in which a transmission member that transmits the driving force from the operating ring 30 and a transmission member that transmits the driving force from the shaft 36 are provided separately, the number of parts can be reduced, and an increase in the size of the endoscope 10 can be suppressed.

Additionally, according to the present embodiment, the shaft 36 is connected to the cam ring 68 via the larger-diameter gear 70 and the smaller-diameter gear 72 serving as the speed reduction mechanism. For this reason, the hardness of the flexible part 20 can be adjusted with a small driving force as compared to a configuration in which the shaft 36 is connected to the cam ring 68 without using the speed reduction mechanism.

Additionally, according to the present embodiment, the hardness adjusting mechanism 50 is constituted of the tightly wound coil spring 52 provided in the insertion part 12, the wire 54 secured to the end part of the tightly wound coil spring 52 on the distal end side, and the movable ring 56 that presses the end part of the tightly wound coil spring 52 on the proximal end side. For this reason, the hardness of the flexible part 20 can be adjusted by fixing the end part of the wire 54 on the proximal end side and pressing the end part of the tightly wound coil spring 52 on the proximal end side by the movable ring 56 to compress the tightly wound coil spring 52.

Other Embodiments

Although the example of the embodiment of the present disclosure has been described above, the present disclosure is not limited to the above embodiment at all, and can be carried out in various modes without departing the spirit of the present disclosure.

For example, the above embodiment is configured to input the driving force of the actuator 32 serving as the external mechanism to the hardness adjusting mechanism 50 via the shaft 36 serving as the second driving force input member. However, the configuration of the external mechanism and the second driving force input member is not limited to the configuration of the embodiment. For example, a configuration in which an operating knob for manual operation other than the operating ring 30 is provided as the second driving force input member may be adopted. In this case, the surgeon can manually operate the operating ring 30 and the operating knob can be manually operated by an assistant or the like other than the surgeon.

Additionally, in the above embodiment, the shaft 36 is connected to the cam ring via the larger-diameter gear 70 and the smaller-diameter gear 72 as the speed reduction mechanism. However, a configuration in which the shaft 36 is connected to the cam ring 68 without using the speed reduction mechanism may be adopted.

Additionally, the configuration of the cam ring 68 (transmission member), which transmits the driving forces from the operating ring 30 and the shaft 36, to the hardness adjusting mechanism 50, is not limited to the embodiment. For example, in a case where the tightly wound coil spring 52 of the hardness adjusting mechanism 50 is repeatedly used, the natural length of the tightly wound coil spring 52 (that is, a length in a state where no external force is applied) may change due to plastic deformation caused by metal fatigue. For this reason, a configuration may be adopted in which an adjusting mechanism for adjusting the length of the tightly wound coil spring 52 is provided in the cam ring 68.

Figure 7:
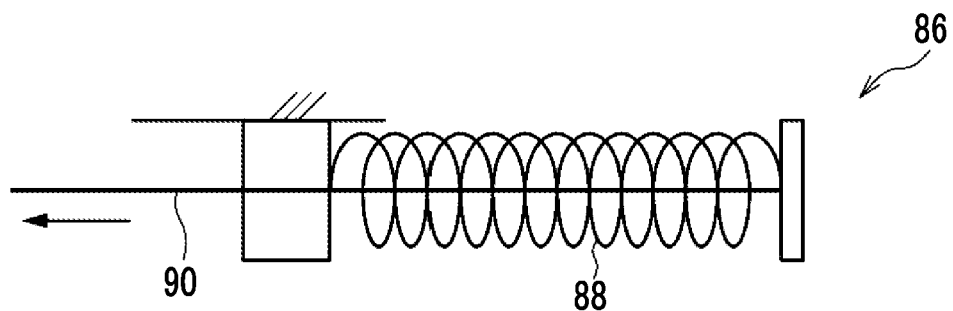
FIG. 7 is a schematic view schematically illustrating a hardness adjusting mechanism of an endoscope according to a first modification example.

Additionally, the above embodiment is configured such that the tightly wound coil spring 52 is compressed by securing the tightly wound coil spring 52 of the hardness adjusting mechanism 50 and the distal end of the wire 54 to each other and fixing the proximal end of the wire 54 to press the proximal end of the tightly wound coil spring 52. However, for example, as illustrated in FIG. 7, the tightly wound coil spring 88 may be compressed by securing the tightly wound coil spring 88 of the hardness adjusting mechanism 86 and the distal end of the wire 90 to each other and fixing the proximal end of the tightly wound coil spring 88 to pull the proximal end of the wire 90.

Moreover, in the above embodiment, the shaft 36 serving as the second driving force input member is connected to the cam ring 68 (transmission member) that transmits the driving force, which is input from the operating ring 30 serving as the first driving force input member, to the hardness adjusting mechanism 50. However, the driving force from the first driving force input member and the driving force from the second driving force input member may be independently transmitted to the hardness adjusting mechanism without using the cam ring 68.

Figure 8:
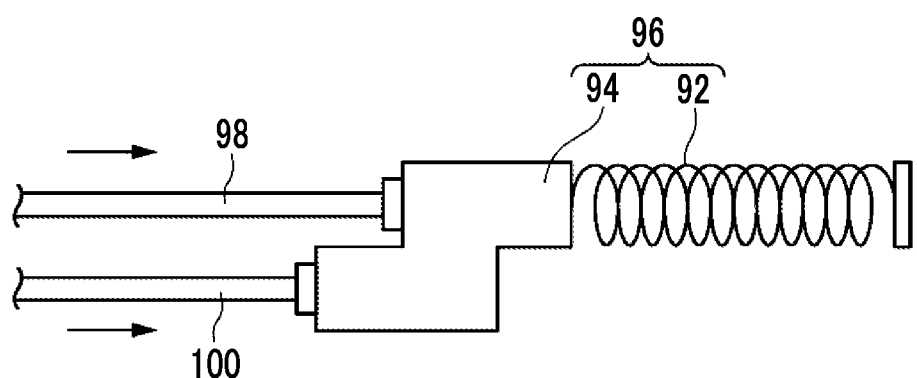
FIG. 8 is a schematic view schematically illustrating a hardness adjusting mechanism of an endoscope according to a second modification example.

Specifically, for example, as illustrated in FIG. 8, the hardness adjusting mechanism 96 may be constituted of the tightly wound coil spring 92 having a fixed distal end and a pressing member 94 that presses the proximal end of the tightly wound coil spring 92. In this case, the tightly wound coil spring 92 can be compressed by pressing the pressing member 94 by a first shaft 98 serving as the first driving force input member and a second shaft 100 serving as the second driving force input member.

Figure 9:
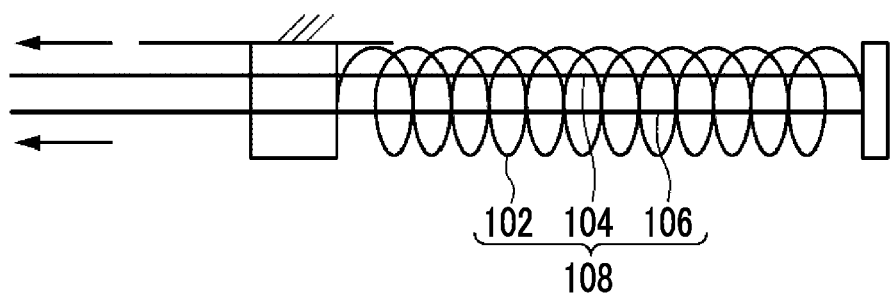
FIG. 9 is a schematic view schematically illustrating a hardness adjusting mechanism of an endoscope according to a third modification example.

Additionally, for example, as illustrated in FIG. 9, the hardness adjusting mechanism 108 may be constituted of a tightly wound coil spring 102 having a fixed proximal end, and a first wire 104 and a second wire 106 fixed to the distal end of the tightly wound coil spring 102. In this case, the tightly wound coil spring 102 can be compressed by pulling the first wire 104 by the first driving force input member and pulling the second wire 106 by the second driving force input member.

EXPLANATION OF REFERENCES

10: endoscope
12: insertion part
14: operating part
16: distal end part
18: bending part
20: flexible part
22: bending piece
24: pin
26: operating knob 28: lock
30: operating ring (example of first driving force input member)
30A: key groove
32: actuator (example of external mechanism)
32A: drive shaft
34: connection interface
34A: insertion hole
36: shaft (example of second driving force input member)
38: forceps port
40: suction button
42: air/water supply button
44: universal cord
46: connector
48: processor device
50: hardness adjusting mechanism
52: tightly wound coil spring
54: wire
56: movable ring (example of movable member)
56A: holding groove
58: fixing metal fitting
60: sleeve
62: sleeve
64: second bending operating mechanism
66: support frame
68: cam ring (example of transmission member)
68A: key
70: larger-diameter gear (example of speed reduction mechanism)
72: smaller-diameter gear (example of speed reduction mechanism)
74: linear groove
76: first cam pin
78: pin hole
80: first cam groove
82: second cam pin
84: second cam groove
86: hardness adjusting mechanism
88: tightly wound coil spring
90: wire
92: tightly wound coil spring
94: pressing member
96: hardness adjusting mechanism
98: first shaft
100: second shaft
102: tightly wound coil spring
104: first wire
106: second wire
108: hardness adjusting mechanism

What is claimed is:

1. An endoscope comprising:
an insertion part having a flexible part;
an operating part continuously provided on a proximal end side of the insertion part;
a hardness adjusting mechanism, comprising a coil spring, that is provided from the operating part to the flexible part and adjusts the hardness of the flexible part;
a first driving force input member that is provided in the operating part and is manually operated and inputs a driving force to the hardness adjusting mechanism; and
a second driving force input member that is provided separately from the first driving force input member and inputs a driving force to the hardness adjusting mechanism,
wherein the first driving force input member and the second driving force input member are simultaneously coupled to the hardness adjusting mechanism.

2. The endoscope according to claim 1, further comprising:
a connection interface to which an external mechanism, which inputs a driving force to the second driving force input member, is attachably and detachably connected.

3. The endoscope according to claim 2,
wherein the first driving force input member is manually operable regardless of whether or not the external mechanism is connected to the connection interface.

4. The endoscope according to claim 3,
wherein the external mechanism is an actuator.

5. The endoscope according to claim 2, further comprising:
a transmission member that transmits the driving force, which is input from the first driving force input member, to the hardness adjusting mechanism,
wherein the second driving force input member is connected to the transmission member.

6. The endoscope according to claim 5,
wherein the second driving force input member is a shaft, and
wherein the shaft is connected to the transmission member via a speed reduction mechanism that reduces the driving force from the external mechanism.

7. The endoscope according to claim 5,
wherein the hardness adjusting mechanism includes:
the coil spring which is a tightly wound coil spring provided in the insertion part;
a wire inserted into the tightly wound coil spring and secured to a distal end of the tightly wound coil spring; and
a movable member that is engaged with the transmission member and compresses the tightly wound coil spring by separating a proximal end of the tightly wound coil spring and a proximal end of the wire from each other.

8. The endoscope according to claim 7,
wherein the tightly wound coil spring is compressed by fixing the proximal end of the wire and pressing the proximal end of the tightly wound coil spring by the movable member.

* * * * *